United States Patent
Peterson

Patent Number: 5,284,442
Date of Patent: Feb. 8, 1994

[54] TOOTH CAPS AND ARTIFICIAL TEETH AND THE METHOD OF FORMING SAME

[76] Inventor: Ken N. Peterson, P.O. Box 18102, Reno, Nev. 89511

[21] Appl. No.: 886,025

[22] Filed: May 20, 1992

[51] Int. Cl.⁵ .................................. A61C 5/10
[52] U.S. Cl. ........................................ 433/223
[58] Field of Search .............. 433/222.1, 223, 208

[56] References Cited

U.S. PATENT DOCUMENTS

| | | | |
|---|---|---|---|
| 3,934,348 | 1/1976 | Janjic | 433/223 X |
| 4,358,271 | 11/1982 | Sperner et al. | 433/223 X |
| 4,426,404 | 1/1984 | Shoher et al. | 433/223 X |
| 4,556,389 | 12/1985 | Ueno et al. | 433/223 X |
| 4,661,071 | 4/1987 | Bell et al. | 433/223 |
| 4,806,383 | 2/1989 | Poltz | 433/223 X |
| 4,980,124 | 12/1990 | Dimmer | 433/223 X |
| 5,049,076 | 9/1991 | Ohno | 433/223 X |
| 5,131,847 | 7/1992 | Ijuin | 433/223 |

*Primary Examiner*—Gene Mancene
*Assistant Examiner*—Nicholas D. Lucchesi
*Attorney, Agent, or Firm*—Herbert C. Schulze

[57] ABSTRACT

Caps for teeth and artificial teeth such as used in bridges, and the like, formed by a method comprising a combination of steps in joining various materials to make the article, wherein the principal difference in the steps as compared to customary techniques is the elimination of a sandblasting operation on a metal base and utilization of a special adhesive to join the other materials to the metal base.

4 Claims, 2 Drawing Sheets

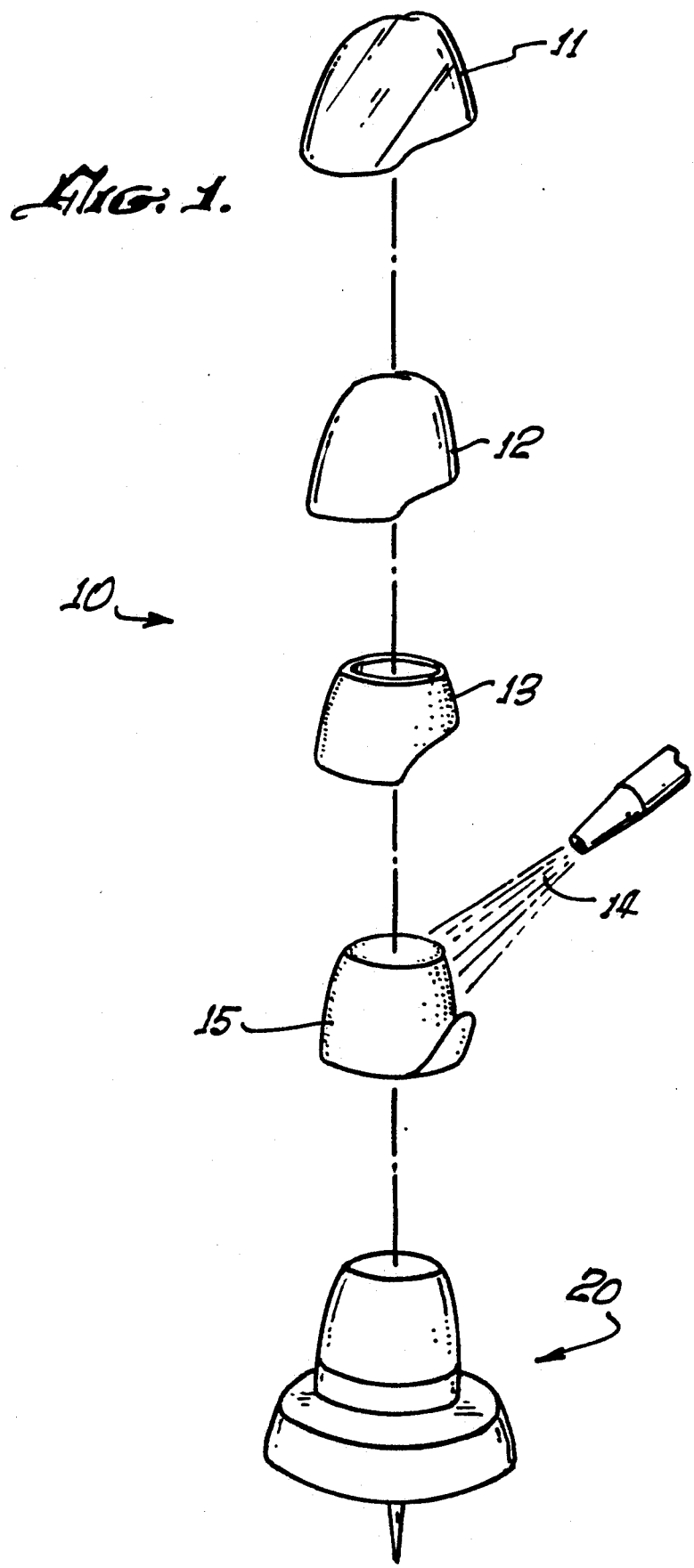

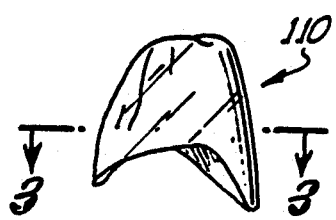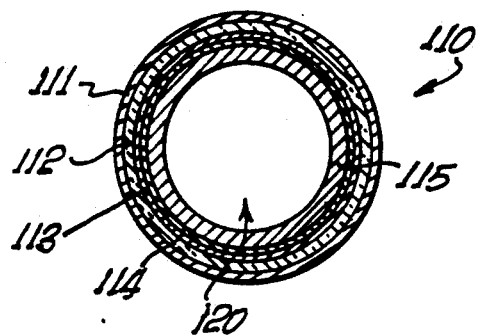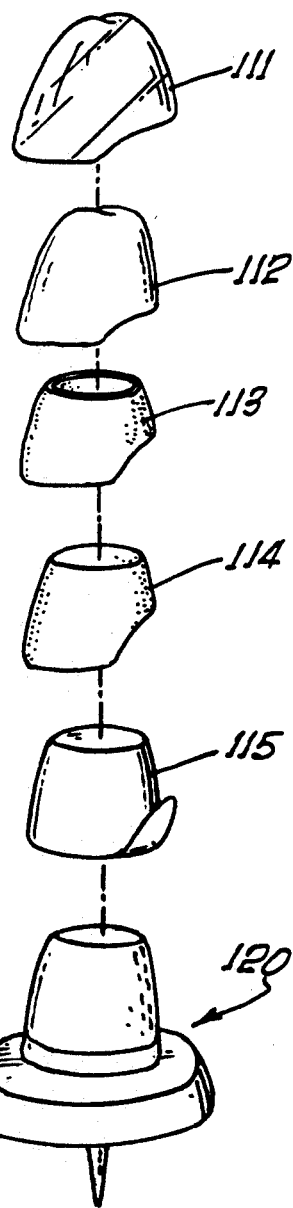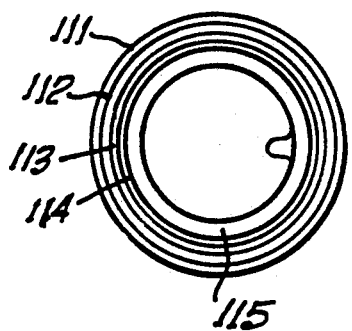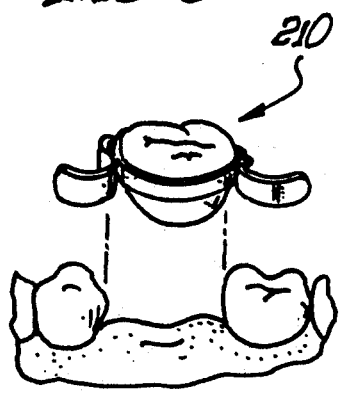

TOOTH CAPS AND ARTIFICIAL TEETH AND THE METHOD OF FORMING SAME

CROSS REFERENCE TO RELATED PATENT APPLICATIONS

There are no patent applications filed by me related to this application.

BACKGROUND OF THE INVENTION

I. Field of the Invention

This invention is in the general field of artificial teeth or caps for teeth, and the like; the invention is more particularly directed to a method wherein a customary step of sandblasting a metal base for the article is eliminated and a special adhesive material is utilized to enhance the joining of materials for a longer life for the articles.

II. Description of the Prior Art

There is no prior art known to me as to the unique elimination of one step considered crucial in the making of articles of this nature and the additional step of utilizing a special adhesive which has, heretofore, been generally deemed to be impossible.

SUMMARY OF THE INVENTION

Artificial teeth and caps for existing teeth which have been damaged or the like are in very wide use.

Such teeth and caps are customarily formed of a number of different materials with a porcelain, or the like, exterior surface. The exact combination of elements and steps used to form such caps and teeth at present are described in detail in the description of a preferred embodiment which follows.

Such articles formed in the present customary manner generally have a useful life of between two and five years. After the period of two to five years, such caps and teeth will crack and require replacement. This results in discomfort and expense to the user.

In recognition of this problem, arrangements have been made between the American Dental Society and certain insurance carriers to cover the loss by insurance up to the five year period. After that, the loss must totally be borne by the user of the article.

I have studied this problem at great length and have made developments of different methods in which to form these articles so as to increase their useful life substantially.

I conceived a unique change in the customary method of making such articles. This change includes the elimination of one generally used, and believed critical, step in the manufacture of such articles. This step, which I have eliminated, is the sandblasting of a metal base upon which the other materials, culminating in the porcelain outer surface, are placed.

I have further enhanced the articles by adding a special adhesive to the unsandblasted metal base which causes excellent adherence of other materials.

Although I do not know exactly why this causes a superior article to be formed, I believe it is because stresses have been relieved in the metal base, and other materials, which stresses are inherent because of the sandblasting and the temperature under which the articles are formed. Some of the stresses are due to differences in rates of thermal expansion of the various materials. The special bonding and sealing material, which I am using in my new method as indicated more completely in the description of a preferred embodiment which follows, assures a properly degassed metal base as described. This combination results in the superior quality which is found.

I have conducted tests on this system in excess of 10 years with no failures in a very extensive number of tests on different articles of this nature.

It is an object of this invention to form artificial teeth, tooth caps, and the like, in a manner such that superior articles are produced having a much greater useful life than articles formed by the heretofore known methods.

Another object of this invention is to simplify and standardize the method of making articles of the nature described.

Another object of this invention is to control the stresses formed upon the materials used in making articles of the nature described.

The foregoing and other objects and advantages of this invention will become apparent to those skilled in the art upon reading the description of a preferred embodiment, which follows, in conjunction with a review of the appended drawings.

BRIEF DESCRIPTION OF THE DRAWINGS

FIG. 1 is an exploded view illustrating the materials utilized in the heretofore known method of forming a tooth cap, or the like, including a view of the sandblasting operations normally used in the past. This figure can be considered the figure illustrating the prior art.

FIG. 2 is a perspective view of a tooth cap made by the method of this invention;

FIG. 3 is an enlarged section on 3—3 of FIG. 2;

FIG. 4 is an exploded view of the elements and steps utilized in the method of this invention;

FIG. 5 is an enlarged bottom plan view of the item of FIG. 2; and

FIG. 6 is a perspective of a bridge utilizing an article produced by the method of this invention to be placed in an area where a tooth is missing.

DESCRIPTION OF A PREFERRED EMBODIMENT

Tooth caps are utilized by dentists for purposes of protecting and beautifying the decayed teeth or damaged teeth. A dentist will grind a good deal of the tooth enamel away on a bad tooth and then will use the cap which is formed in the manner hereinafter described for covering the remaining portion of the tooth and keeping it healthy. If it was not capped the tooth would continue to decay and would cause discomfort as well as considerable potential health problems.

When the tooth has been ground away to the point where the dentist is satisfied with what he has left of the tooth, the dentist makes an impression of what is left and this then becomes the basis for a cap to be prepared. The mold is made and then a casting is made within that mold which represents the tooth upon which a cap must fit.

A cap is frequently referred to as a crown and it may be that the words will be used interchangeably.

Dentist's impression material is generally of a rubber base material known to those skilled in the art. When the impression has been taken, the interior of the impression mold will be a perfect impression of the tooth in the patient's mouth.

A material known as "dental stone" is then poured into this impression. This is a material which will neither expand nor shrink, in order that an exact duplicate of the tooth to be capped is achieved. The dentist will have ceased his grinding or preparation of the tooth in most cases adjacent the gum of the patient. The crown will be formed as hereinafter shown in such a manner that the metal base of the crown, or cap, which is described, will terminate at the margin area which is the area around the tooth at the gum.

A metal base is made upon the stone impression by heating the metal and centrifugely casting it. This step is known to those skilled in the art and is illustrated in the prior art in FIG. 1 wherein the base or stone impression to duplicate the tooth in the patient's mouth is indicated at 20 with the metal cap 15 shown after it has been cast. At 14 the metal is customarily sandblasted with aluminum oxide or the like. Thereafter an opaque porcelain material 13 is baked on to the metal cap 15 after which a further porcelain material 12 is fired over the opaque porcelain 13. The final step consists of applying the glaze 11 and properly firing that.

Frequently in this operation there will be potential of gas forming in the metal object 15. Any leakage of gas will cause the rest of the item, the porcelain, to crack.

A cap shown as made by my invention at FIG. 2 will appear on the exterior the same as any other crown. However, as will be seen, it has been formed in a different manner and therein lies the invention and the elimination of cracking which normally takes place in two to five years.

FIG. 2 illustrates the completed crown generally 110. The elements making it up are the metal base 115, a sealing and bonding agent 114, (one such material is described in U.S. Pat. No. 2,852,054) the opaque porcelain 113, the finish porcelain 112, and the glaze 111. Each of these items is shown as it finally exists in greatly enlarged detail in both FIGS. 5 which is a bottom view and in FIG. 3 which is sectional view. It is to be understood that the sectional view is indicated as round, as is the bottom view. Also the entire item is indicated as being perfectly round in its various sections. This of course is not necessarily true as most teeth will not be round, but will be in varying shapes. A round crown could be made in this manner and the steps will be exactly the same regardless of the shape of the tooth remaining in the patient's mouth and regardless of the shape of the final exterior.

FIG. 6 illustrates a bridge with what is referred to in the trade as a "pontic" or a dummy tooth 210 which is then fastened to two adjacent teeth. It ma be fastened to the two adjacent teeth in many different ways, known to those skilled in the art, and this will not be detailed. However, my method of making a crown or a cap is also used in making the pontic or dummy tooth, and it is for this reason that it is shown.

The various steps in the manufacture of a crown or a pontic according to the prior art are well known to those skilled in the art and a detailed description is unnecessary. However, such detailed description may be found, for example, in various dental publications, one of which is found in the Instructional Booklet entitled "Fabrication Procedures for Dental Prosthetic Devices" published by the National Association of Dental Laboratories, 3801 Mount Vernon Avenue, Alexandria, Va. 22035, especially at pages 71 through 75. This publication, for example, follows the technique illustrated as prior art herein. The complete detail of each step is not indicated, since it will be known to those skilled in the art. However, the crucial steps in my new method which are different any known method include (1) the elimination of any blasting of the metal coping with aluminum oxide, or the like, and, (2) the application to the metal coping of the bonding agent or sealing agent to seal any and all crevices which may exist. The way this is handled is such that the coping will be fired to a high temperature in an appropriate furnace or kiln to approximately 1975 degrees fahrenheit. This temperature tends to remove gasses, or "degas" the metal. After the metal has cooled to room temperature, a very thin layer of the bonding agent or sealing agent is applied over the coping where the coping is to receive the porcelain. This bonding agent or sealer seals off all crevices made by the grinding stones which are used so that no air will escape and no bubbles will exist. Thus, a proper bond of the porcelain in the later stages will occur. This is really the secret of this invention, and something heretofore thought impossible.

After the bonding or sealing agent has been brushed on, the coping is placed back into a furnace or kiln and fired to a temperature of 1925 degrees (note this is slightly less than the original copying temperature). When it reaches this temperature, it is held at that temperature under a vacuum for a total of two and one half minutes to assure that the sealer has properly sealed. Once again the coping is removed from the furnace or kiln and cooled, preferably to room temperature. After that, it is then used as a base upon which to apply the opaque underlay or porcelain material. From this step on the procedure now follows the standard procedure as generally used.

Indicative of the uniqueness of this operation is the fact that the various alloys used are supplied by manufacturers who particularly state that the procedure I have discovered is not correct. For example a widely used material known as "Micro-Star" as manufactured by Pennwalt Jelenko Dental Health Products states on the package as follows "DEGASSING: Raise temperature from 1300 degrees F (704 degrees C) to 1650 degrees F (1010 degrees C) without vacuum.—Sandblast with clean quartz or aluminum oxide abrasive. Do not use metal conditioners".

While the embodiment of this invention described above is fully capable of achieving the objects and advantages desired, it is to be understood that this embodiment has been shown and described for purposes of illustration only, and not for purposes of limitation.

I claim:

1. The method of forming an artificial tooth or crown for a tooth utilizing a metal coping as a base wherein, after being formed, the metal coping is heated to a temperature of approximately 1975 degrees fahrenheit; the coping is then cooled; a metal surface sealer is applied to the cooled coping; the coping with the metal sealer thereon is then heated to approximately 1925 degrees fahrenheit under vacuum and held at this temperature for two and one half minutes; the metal coping with its sealing agent is allowed to cool.

2. The method of claim 1 wherein after cooling of the metal coping and sealed, the metal coping with sealer is then coated with an opaque porcelain material, and further coatings and heatings thereof are applied and performed in a customary manner.

3. The method of claim 1 wherein no sandblasting of the metal coping is used.

4. The method of claim 1 wherein no abrasive particle blasting of the metal coping is used at any stage.

* * * * *